US007672706B2

(12) United States Patent
Sathyanarayana

(10) Patent No.: US 7,672,706 B2
(45) Date of Patent: Mar. 2, 2010

(54) SYSTEMS AND METHODS FOR MEASURING PULSE WAVE VELOCITY WITH AN INTRAVASCULAR DEVICE

(75) Inventor: Shashidhar Sathyanarayana, Union City, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 982 days.

(21) Appl. No.: 10/924,428

(22) Filed: Aug. 23, 2004

(65) Prior Publication Data
US 2006/0058653 A1 Mar. 16, 2006

(51) Int. Cl.
*A61B 5/05* (2006.01)
(52) U.S. Cl. ................... 600/407; 600/505
(58) Field of Classification Search .......... 600/437, 600/438, 481, 485, 500, 407, 486, 488, 504, 600/505
See application file for complete search history.

(56) References Cited

U.S. PATENT DOCUMENTS

| 4,501,277 | A | * | 2/1985 | Hongo | ........................ 600/441 |
| 4,757,821 | A | | 7/1988 | Snyder et al. | |
| 4,768,515 | A | * | 9/1988 | Namekawa | ................. 600/455 |
| 5,125,410 | A | * | 6/1992 | Misono et al. | .............. 600/463 |
| 5,156,157 | A | * | 10/1992 | Valenta et al. | .............. 600/463 |
| 5,305,745 | A | * | 4/1994 | Zacouto | ....................... 600/324 |
| 5,363,853 | A | | 11/1994 | Lieber et al. | |
| 5,453,575 | A | | 9/1995 | O'Donnell et al. | |
| 5,682,896 | A | | 11/1997 | Scheib et al. | |
| 5,701,898 | A | | 12/1997 | Adam et al. | |
| 5,921,936 | A | | 7/1999 | Inukai et al. | |
| 5,931,790 | A | | 8/1999 | Peel, III | |
| 5,967,987 | A | | 10/1999 | Sumanaweera et al. | |
| 5,989,191 | A | | 11/1999 | Scampini | |
| 6,120,442 | A | * | 9/2000 | Hickey | ........................ 600/300 |
| 6,165,128 | A | * | 12/2000 | Cespedes et al. | ............ 600/463 |
| 6,176,832 | B1 | * | 1/2001 | Habu et al. | ................... 600/485 |
| 6,261,233 | B1 | | 7/2001 | Kantorovich | |
| 6,354,999 | B1 | | 3/2002 | Dgany et al. | |
| 6,503,205 | B2 | | 1/2003 | Manor et al. | |

(Continued)

FOREIGN PATENT DOCUMENTS

EP 0253687 A 1/1988

OTHER PUBLICATIONS

Mitchell et al, Comparison of techniques for measuring pulse-wave velocity in the rat, 1997, the American Physiological Society, pp. 203-210.*

*Primary Examiner*—Long V Le
*Assistant Examiner*—Jacqueline Cheng
(74) *Attorney, Agent, or Firm*—Darby & Darby P.C.; Patrick R. Turner

(57) ABSTRACT

The systems and methods described herein allow measurement of the velocity of a pulse wave propagating within a body lumen using an intravascular elongate medical device. The elongate medical device can include a data collection device configured to collect pulse wave data at a location within the lumen. The data collection device is communicatively coupled with a velocity measurement system and configured to output the collected data to the velocity measurement system. The velocity measurement system is configured to calculate the velocity of the pulse wave based on the collected data. The velocity of a pulse wave over a region of the lumen can be used for tissue characterization, diagnosis and the like.

37 Claims, 8 Drawing Sheets

U.S. PATENT DOCUMENTS

| | | | |
|---|---|---|---|
| 6,511,436 B1 * | 1/2003 | Asmar | 600/500 |
| 6,554,774 B1 | 4/2003 | Miele | |
| 6,730,030 B2 | 5/2004 | Palti | |
| 6,758,819 B2 | 7/2004 | Nomura | |
| 2005/0187468 A1 * | 8/2005 | Atlas | 600/437 |

* cited by examiner

SYSTEMS AND METHODS FOR MEASURING PULSE WAVE VELOCITY WITH AN INTRAVASCULAR DEVICE

FIELD OF THE INVENTION

The systems and methods relate generally to measuring the velocity of pulse waves within a body lumen using an intravascular device.

BACKGROUND INFORMATION

Pulse wave velocity refers to the speed of propagation of mechanical waves that travel along the length of a blood vessel. One common example is a cardiac pulse wave generated by the contractions of the heart. If one were to take the pulse of a subject at two well separated locations along the same vessel, there would be a noticeable time delay. This delay results from the amount of time necessary for the cardiac pulse wave to travel the distance between the two locations.

It is well known that the speed of a mechanical wave is dependent on the physical properties of the medium supporting the wave. It has also been realized that pulse wave velocity can vary from point-to-point along a body lumen, such as a blood vessel and the like. It has been proposed that the variation of pulse wave velocity along the length of a blood vessel wall can be used to characterize the blood vessel and serve as an indicator of blood vessel health. Changes in vessel pathology can alter the mechanical properties effecting the velocity of the wave. For instance, variations in stiffness along the length of a vessel could cause changes in velocity. In the case of a cardiac pulse wave, the velocity of the wave can be dependent on the elastic characteristics of the blood vessel wall and surrounding tissue as well as the compressibility of the blood. Currently, however, intravascular diagnostic systems and techniques are not capable of measuring pulse wave velocity within a blood vessel.

Accordingly, systems and methods for measuring pulse wave velocity within a blood vessel with an intravascular device are needed.

SUMMARY

The systems and methods provided herein allow for the measurement of the velocity of a pulse wave within a body lumen using an intravascular device. In one exemplary embodiment, a medical system is provided having an elongate medical device configured for insertion into a body lumen of a living being. The elongate device includes a data collection device configured to collect data on the pulse wave within the body lumen and output the data to a velocity measurement system. The velocity measurement system is communicatively coupled with the data collection device and configured to control the data collection device and calculate the velocity of the pulse wave within the body lumen based on the pulse wave data collected by the data collection device.

Also provided is a method of measuring the velocity of the pulse wave within a body lumen. One example of the method includes collecting pulse wave data with an elongate medical device at a first location within a body lumen, collecting pulse wave data with the elongate medical device at a second location within the body lumen and calculating the velocity of the pulse wave in the region between the two locations with the pulse wave data collected at the two locations.

The systems and methods provided herein can be used with any measurement method including, but not limited to, imaging-based methods, sensor-based methods and the like. In one example of velocity measurement using an imaging-based method, the data collection device is an imaging device and the pulse wave data collected at the first and second locations includes image data of the inner wall of the body lumen. The velocity measurement system can analyze the image data to determine the temporal variation of the size of the lumen wall at the first and second locations and calculate the velocity of the pulse wave based on the temporal variation of the lumen wall.

In an example of velocity measurement using a sensor-based method, the data collection device can be a pressure or displacement sensor and the pulse wave data collected at the first and second locations includes pressure data. The velocity measurement system can analyze the pressure data and calculate the velocity of the pulse wave based on the temporal variation of the pressure within the lumen.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments.

DETAILED DESCRIPTION

The systems and methods described herein allow pulse wave velocity measurement with an intravascular device. A medical system is provided that includes a velocity measurement system and an elongate medical device insertable into the body lumen of a subject. The elongate medical device is configured to collect data that can be used by the velocity measurement system to calculate the velocity of any pulse waves propagating within the lumen. Methods of measuring the pulse wave velocity with the medical system are also provided. This velocity measurement can be used in a diagnosis of the vessel health or to otherwise characterize the blood vessel tissue.

Figure 1:
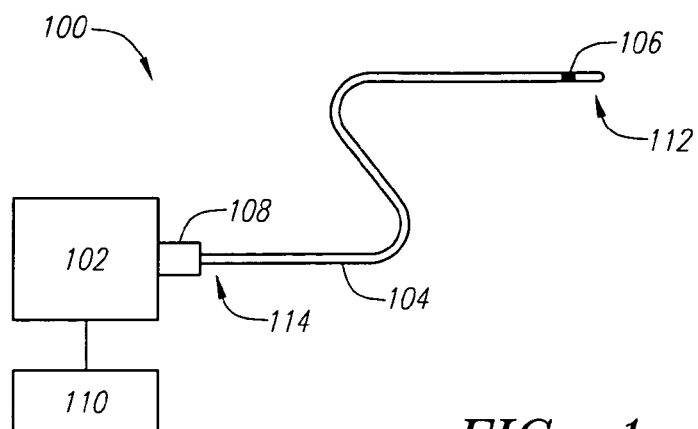
FIG. 1 depicts a schematic view of an exemplary embodiment of medical system for measuring pulse wave velocity.

FIG. 1 depicts an exemplary embodiment of medical system 100 including velocity measurement system 102 and elongate medical device 104, having distal end 112 and proximal end 114. Proximal end 114 is coupled to velocity measurement system 102 via coupler 108. Elongate medical device 104 can be any device configured for insertion into a blood vessel of a living being, such as a catheter, endoscope or the like. To facilitate the description of medical system 100, elongate medical device 104 will be described as a catheter; however, this is merely to facilitate the discussion and is not intended to limit device 104 to any one configuration. Medical system 100 can also optionally include a reference source 110, the use of which will be described in more detail below.

Medical system 100 is preferably configured to measure the velocity of the pulse wave across a desired segment of a body lumen. To make a velocity measurement, distal end 112 of catheter 104 is inserted into proximity with the desired segment of the body lumen. Catheter 104 includes one or more data collection devices 106 to collect pulse wave data at any point along the body lumen. This data is transferred to velocity measurement system 102 for processing. To calculate the velocity over the desired lumen segment, data is preferably collected at two separate locations at opposite ends of the desired segment, although data can be collected in only one location or any number of additional locations, depending on the velocity measurement method used or the needs of the application. Velocity measurement system 102 can then use the collected data to calculate the velocity of the pulse wave propagating between the two locations.

Figure 2:
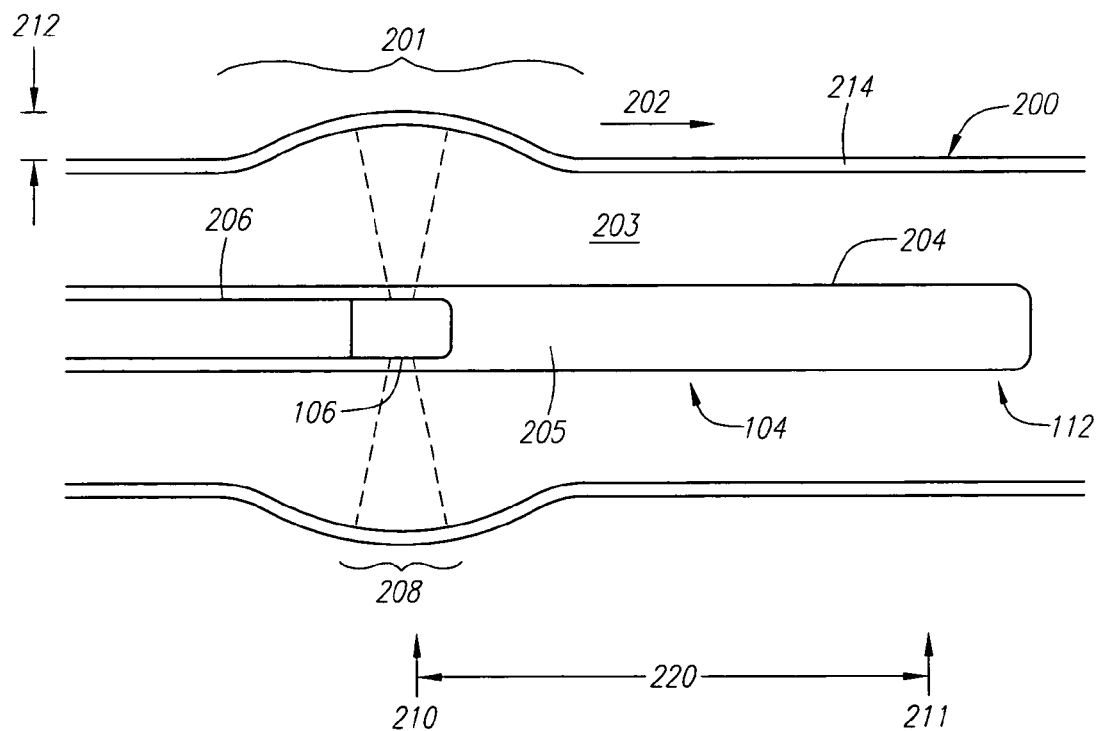
FIG. 2 depicts a schematic view of an exemplary embodiment of an elongate medical device positioned within a blood vessel.

Any desired method of pulse wave velocity measurement can be used with medical system 100. Several exemplary methods, referred to as imaging-based and sensor-based methods, will be discussed herein; however, it should be noted that medical system 100 is not limited to such. In one example of an imaging-based method, images of two or more locations within a blood vessel are taken at known points in time. The images are then examined to determine at what time the pulse wave passes each location. The difference in time can then be used to calculate the velocity of the wave between the two locations. FIG. 2 depicts one exemplary embodiment of medical system 100 configured for use in an imaging-based method of velocity measurement.

In this embodiment, catheter 104 includes elongate tubular member 204 having inner lumen 205. A central core 206 is located within lumen 205 and can be moved, or slid, distally and proximally within the elongate member 204 as desired. Any imaging technique can be used in the imaging-based method, including ultrasound and optical techniques. Accordingly, data collection device 106 can be a rotating ultrasound transducer, an array of transducers, an optical imager or the like depending on the chosen imaging technique. Imaging device 106 is located on the distal end of a central core 206 and communicatively coupled with velocity measurement system 102, for instance via a transmission cable (not shown) located within central core 206. Velocity measurement system 102 preferably includes control hardware and/or software for controlling imaging device 106.

FIG. 2 depicts catheter 104 within body lumen 200 during propagation of cardiac pulse wave 201 in downstream direction 202. Pulse wave 201 is represented by the outwards displacement 212 of walls 214. Body lumen 200 can be any type of blood vessel such as an artery, vein, venule and the like. In this embodiment, system 100 is being used to measure the velocity over region 220 between locations 210 and 211.

At each location 210 and 211, imaging device 106 is preferably configured to image a cross-section 208 of vessel 200 to provide a 360 degree circumferential image of vessel wall 214. A smaller cross-section of vessel wall 214 less than 360 degrees can be used so long as the passage of pulse wave 201 can still be detected. The image data collected from locations 210 and 211 can then be transferred to velocity measurement system 102, which is configured to process the data and calculate the resulting pulse wave velocity.

As mentioned above, medical system 100 can also include reference source 100. Reference source 110 is preferably used as a reference for triggering data collection with imaging device 106. When measuring the velocity of cardiac pulse wave 201, reference source 110 is preferably a heart monitor such as an electrocardiogram (EKG) or the like. Heart monitor 110 is attached to the subject and used to monitor heart activity during the procedure. Heart monitor 110 is preferably communicatively coupled with velocity measurement system 102 such that velocity measurement system 102 can activate imaging device 106 when a heartbeat occurs.

Figure 3:
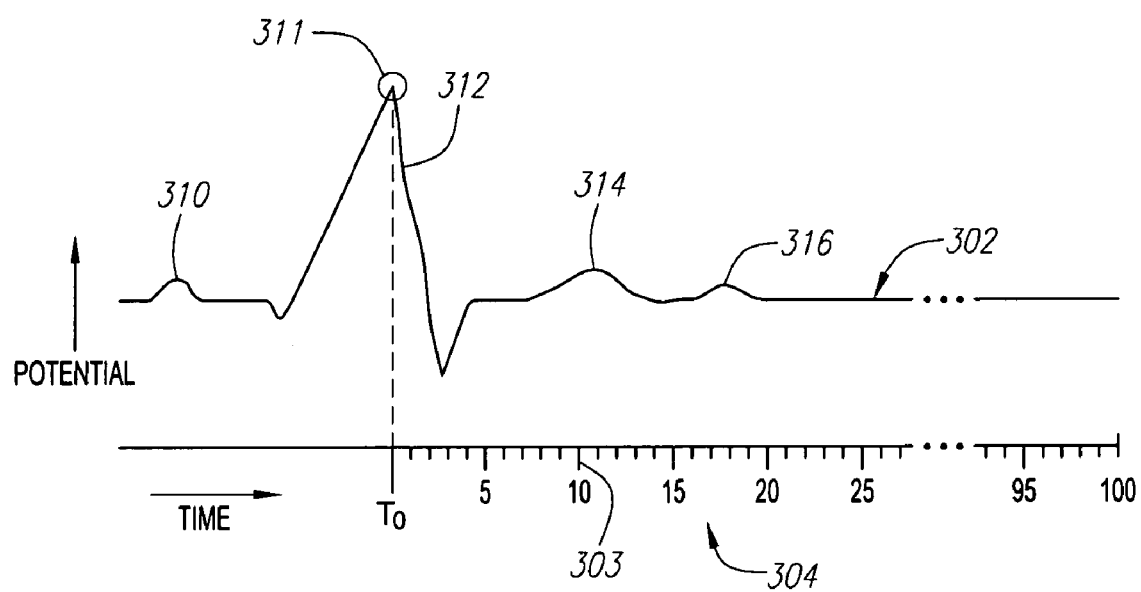
FIG. 3 depicts a plot of an example heart monitor output signal.

FIG. 3 depicts an exemplary heart monitor signal 302 showing the electrical potential of the heart over time during a cardiac cycle. Specifically, heart monitor signal 302 includes P wave 310, QRS complex 312, T wave 314 and U wave 316. Also shown are the times 303 at which imaging device 106 images blood vessel 200. The heart monitor signal 302 is preferably output to velocity measurement system 102 which activates imaging device 106 to image vessel 200. The heart reaches its peak potential at time $T_0$, which corresponds to the creation of pulse wave 201 by the cardiac contraction. Depending on the location of region 220 within the subject's body, a lag time will exist between the creation of the pulse wave and the passage of the pulse wave through region 220. To ensure vessel 200 is being imaged when pulse wave 201 arrives, a sequence 304 of images is collected over a sufficiently long period of time beginning at a predetermined trigger point 311. Trigger point 311 can be any point on heart monitor output 302. For instance, in this embodiment trigger point 311 is the peak potential of heart monitor output 302 occurring at time $T_0$ during QRS segment 312. Once trigger point 311 is detected, velocity measurement system 102 begins activating imaging device 106 for period of time sufficient to image the passage of pulse wave 201.

The period of time and the rate at which images are taken can be adjusted as desired. In one embodiment, imaging device 106 operates at a rate of 30 cross-sectional images per second with a sequence length of 100 images, resulting in one image every 0.0333 seconds. This rate is intended only as an example and, in fact, any sufficient rate can be used. Also, the rate can be variable so that relatively more images are taken during the time when pulse wave 201 is expected to pass. One of skill in the art will recognize a vast number of variation in data collection methods exist and, accordingly, the systems and methods described herein are not limited to any one method.

Preferably, the image data is processed by the velocity measurement system 102 to form images capable of display so that the user can view region 220. For instance, in an exemplary embodiment using ultrasound imaging, transducer 106 outputs a signal to velocity measurement system 102 corresponding to the echo response of the vessel 200. Velocity measurement system 102 preferably includes an imaging system capable of processing the image data into a format suitable for display. FIGS. 4A-D are exemplary cross-sectional images 401-404 of vessel 200 created from image data taken by imaging device 106 during an image collection sequence. In this embodiment, imaging device 106 is a rotational ultrasound transducer and images 401-404 are ultrasound images.

Figure 4A:
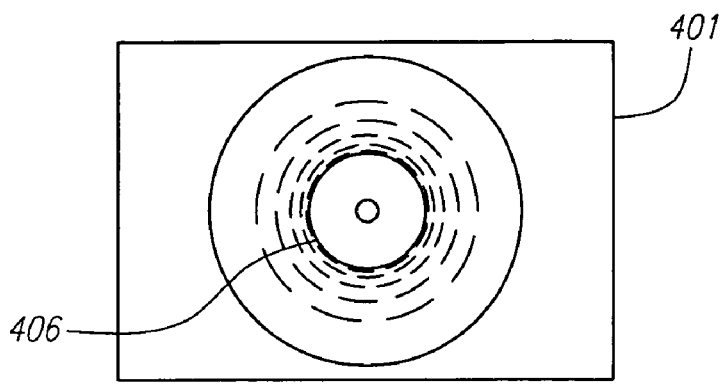
FIGS. 4A-D depict example images of a blood vessel during passage of a pulse wave.
Figure 4B:
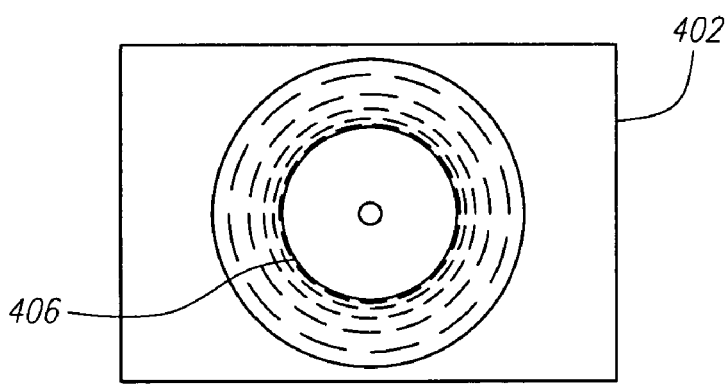
Figure 4C:
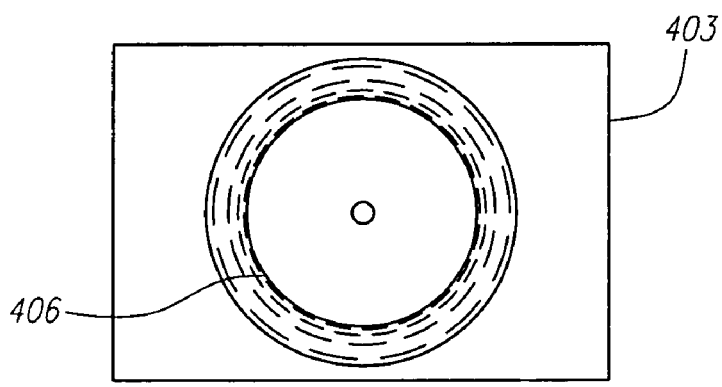
Figure 4D:
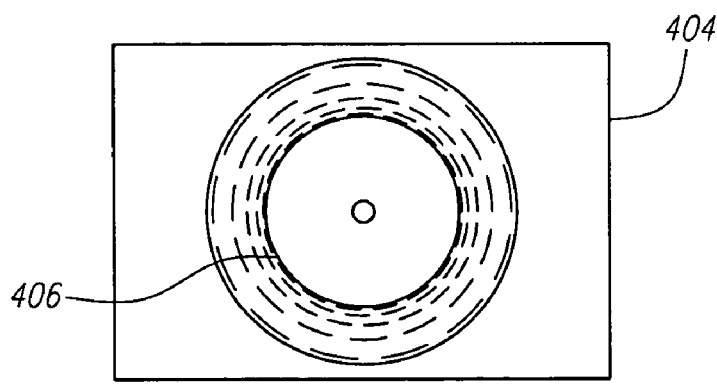

The images 401-404 depicted in FIGS. 4A-D represent a sub-sequence of images selected from the overall image sequence 304. These images 401-404 demonstrate the displacement of vessel wall 214 caused by the passage of pulse wave 201 past first location 210. Using the example imaging sequence discussed with regard to FIG. 3, image 401 depicted in FIG. 4A is representative of the 11$^{th}$ image in a one hundred image sequence, while image 402 depicted in FIG. 4B is representative of the 12$^{th}$ image, image 403 depicted in FIG. 4C is representative of the 13$^{th}$ image and image 404 depicted in FIG. 4D is representative of the 14$^{th}$ image. Each image 401-404 depicts vessel border 406 formed by the intersection between vessel wall 214 and blood 203. Images 401-403 depict the successive displacement of vessel border 406, with border 406 having the greatest size in image 403. Image 404 depicts border 406 once again decreasing in size, which indicates that pulse wave 201 peaked in image 403, or 0.433 seconds after time $T_0$.

Likewise, a similar analysis is performed at location 211 where a sequence of images is taken at known points in time and those images are examined to determine at what point pulse wave 201 peaks. For example, location 211 can be located downstream from location 210 and pulse wave 201 can peak in the 16th image taken within the image sequence, or 0.533 seconds after time $T_0$. This is 0.1 seconds after the time that pulse wave 201 passed location 210. Equation (1) below shows the well known relation between velocity (V), distance (D) and time (T).

$$V = \frac{D}{T} \quad (1)$$

If the distance separating locations 210 and 211 is one centimeter, the resulting velocity of wave 201 is calculated to be one meter per second (M/s). This is a simple but effective method of calculating pulse wave velocity. However, medical system 100 can be used with any desired velocity calculation method. For instance, an analysis of the temporal variation in size of border 406 at location 210 allows the determination of an associated Fourier spectrum. A similar analysis of border 406 at location 211 allows a determination of the change in phase at each frequency, which translates into a velocity measurement. Because pulse wave echoes and noise are typically present in vessel 200, calculation of the velocity at each frequency allows more reliable and accurate conclusions on the state of the vessel tissue to be made.

The calculated pulse wave velocity in region 220 can then be used for any desired purpose. The pulse wave velocity can be used as a direct indicator of vessel pathology or to highlight the vessel for further study or investigation. Also, the pulse wave velocity can serve as an independent component in the space of all features used in tissue characterization. The pulse wave velocity can also be used to determine the value of Young's modulus for region 220 according to equations (2) or (3) below:

$$c_o = \sqrt{\frac{Eh}{2R\rho}} \quad (2)$$

$$c_o = \sqrt{\frac{Eh}{2R\rho(1-v^2)}} \quad (3)$$

where $c_o$ is the wave velocity, E is Young's modulus, h is the thickness of the vessel wall 214, R is the radius of the vessel, $\rho$ is the mass density of the blood 203 and v is Poisson's ratio.

Velocity measurement system 102 is preferably configured to perform any image analysis required by the application. In one embodiment, velocity measurement system 102 includes an image analysis software application that can operate in conjunction with the imaging system. The image analysis software can process the image data in any desired format and locate and analyze the change in border 406. One of skill in the art will recognize that numerous methods of image analysis exist and accordingly, velocity measurement system 102 is not limited to any one method. Alternatively, the collected images 401 can be analyzed manually by an operator to determine which image 401 depicts the passage of wave 201. This image 401 can then be identified to the velocity measurement system 102 for use in the velocity calculation.

Figure 5:
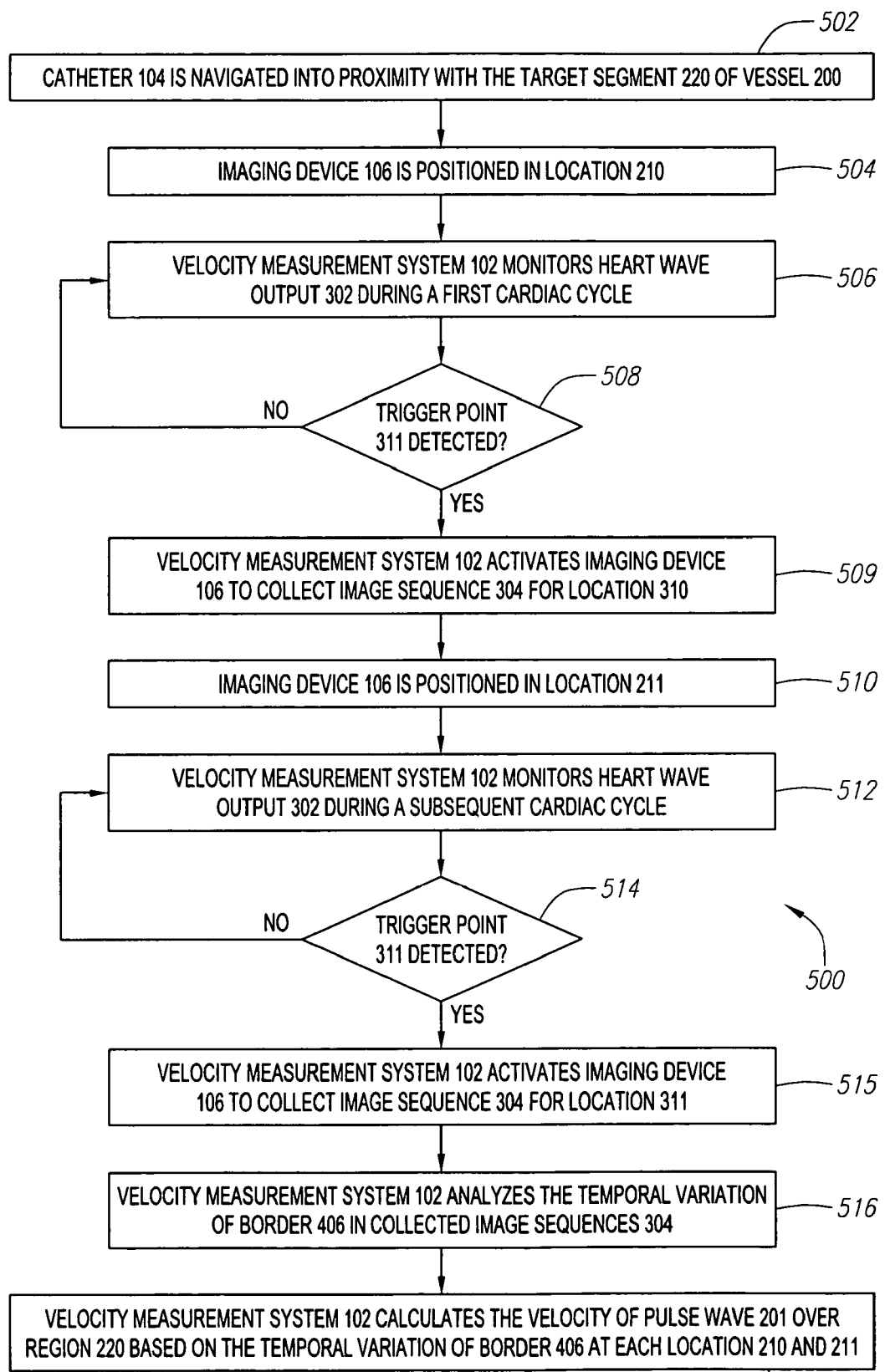
FIG. 5 depicts a flow chart of an example method of measuring pulse wave velocity with an imaging-based method.

FIG. 5 is a flow chart depicting one exemplary embodiment of an imaging-based velocity measurement method 500. At 502, catheter 104 is navigated into proximity with the target segment 220 of vessel 200, i.e., the portion of vessel 200 to be characterized with a pulse wave velocity measurement. Then, at 504, imaging device 106 is positioned in location 210 by sliding central core 206 in a proximal or distal direction as necessary. At 506, velocity measurement system 102 monitors heart wave output 302 during a first cardiac cycle. At 508, system 102 checks for trigger point 311 during the first cardiac cycle. If trigger point 311 has not occurred then system 102 proceeds back to 506. If trigger point 311 has occurred, system 102 proceeds to 509 and activates imaging device 106 to collect image sequence 304. Next, at 510, catheter 104 is advanced, if necessary, and imaging device 106 is positioned in location 211. At 512, velocity measurement system 102 monitors heart wave output 302 during a subsequent cardiac cycle. At 514, system 102 checks for trigger point 311 during the first cardiac cycle. If trigger point 311 has not occurred then system 102 proceeds back to 512. If trigger point 311 has occurred, system 102 proceeds to 515 and activates imaging device 106 to collect image sequence 304. Then, at 516, velocity measurement system 102 analyzes the temporal variation of border 406 within the collected image sequences 304. Finally, at 518, velocity measurement system 102 calculates the velocity of pulse wave 201 over region 220 based on the temporal variation of border 406 at each location 210 and 211.

Velocity measurement system 102 can be configured to calculate the pulse wave velocity along a longitudinal axis of region 220, such as the central longitudinal axis of vessel 200. Alternatively, velocity measurement system 102 can be configured to calculate the pulse wave velocity along the circumference of region 220. Velocity variations along the circumference of region 220 can provide the user information on the various locations distributed radially around vessel 200. In all cases the velocity calculations or measurements can be visually mapped to display to the user.

In method 500, the user collects image data at locations 210 and 211 separately during different cardiac cycles. Thus, the velocity calculation is based on measurements taken from separate pulse waves 201. To maintain consistent velocity measurements, the subject's physiological and cardiac condition should be kept relatively stable during method 500. A rapidly varying heart rate or blood pressure, for example, can alter the velocity of pulse wave 201 from one cardiac cycle to the next and introduce uncertainty into the collected data. Also, data can be collected in each location 210 and 211 over multiple cardiac cycles if desired. In one embodiment, the data is averaged together to form a baseline value at each location, while in another embodiment the data is compared to other physiological conditions of the subject to determine the optimum data set(s) for use in the velocity calculation.

In the above embodiments, location 211 is downstream from location 210, and data is collected from location 211 after location 210. It should be noted that the order in which the various locations are visited for collecting data can be varied and data can be collected from the downstream location 211 prior to the upstream location 210. Furthermore, as one of skill in the art will readily recognize, data can be collected from any number of additional locations to measure the velocity in as many regions 220 of vessel 200 as desired.

Figure 6A:
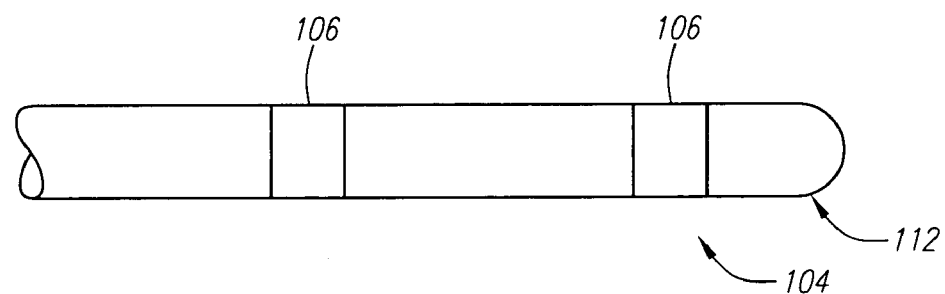
FIG. 6A depicts a schematic view of another exemplary embodiment of an elongate medical device.

In order to allow the collection of data from multiple locations, catheter 104 can include more than one data collection devices 106. FIG. 6A depicts an exemplary embodiment of catheter 104 having two data collection devices 106. This embodiment can allow the collection of data at locations 210 and 211 without the need to readjust the location of catheter 104 or data collection devices 106. This embodiment can also allow data collection using the same pulse wave 201. Use of the same pulse wave 201 eliminates the risk of data corruption associated with variances in the physiological condition of the subject, as described above. Preferably, data collection devices 106 are separated by a known distance 602, although this distance is not required to be fixed.

Figure 6B:
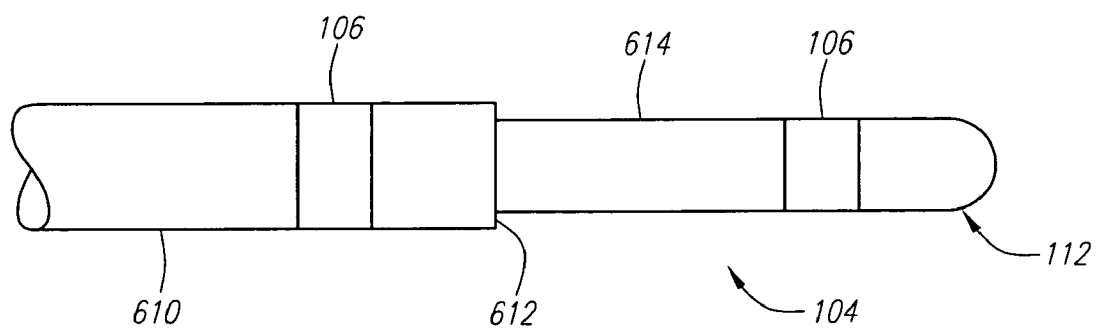
FIG. 6B depicts a schematic view of another exemplary embodiment of an elongate medical device.

One of skill in the art will readily recognize that data collection devices 106 can be placed on separate telescoping sections of catheter 104 as depicted in FIG. 6B, to allow variation of the distance 602 between data collection devices 106. In this embodiment, an outer elongate tubular section 610 has an open distal end 612, through which an inner elongate section 614 can adjustably extend. Each section preferably has a data collection device 106 located thereon. The data collection device 106 located on outer elongate section 610 is preferably configured to allow for the telescoping movement of inner elongate section 614.

The embodiments depicted in FIGS. 6A-B can be used in with any data collection method, including imaging-based and sensor-based methods. With sensor-based method 700, each of the data collection devices 106 is preferably a pressure or displacement sensor configured to detect the passage of pulse wave 201. In one embodiment, each sensor 106 is preferably controlled by velocity measurement system 102, which instructs sensor 106 to measure the pressure within vessel 200 and output the results to velocity measurement system 102, which records the measurement. Velocity measurement system 102 can also record the time at which the measurement was taken, or system 102 can operate sensor 106 to take a sequence of pressure measurements.

Figure 7:
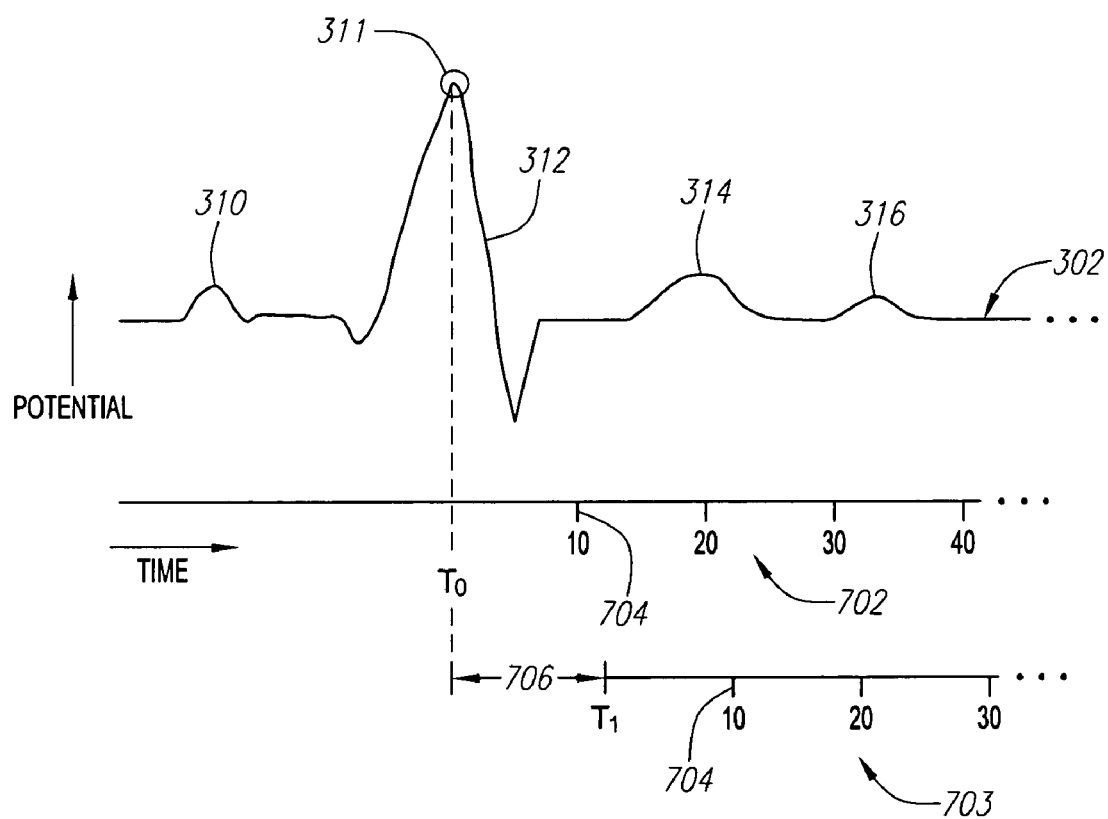
FIG. 7 depicts a plot of another example heart monitor output signal.

FIG. 7 depicts exemplary heart monitor signal 302 including P wave 310, QRS complex 312, T wave 314 and U wave 316. Data sequence 702 is collected at upstream location 210 and data sequence 703 is collected at downstream location 211. The collection of data sequence 702 begins upon the occurrence of trigger point 311 at time $T_0$, while the collection of data sequence 703 is delayed by time period 706 until time $T_1$. The length of time period 706 is preferably chosen to compensate for the delay caused by the propagation of pulse wave 201 from location 210 to 211 and allow sequence 703 to occur over the time period when pulse wave 201 is most likely to pass. Each measurement 704 in sequences 702-703 can be taken at fixed or variable intervals.

Velocity measurement system 102 can be configured to examine the pressure measurements from each location and calculate the velocity of wave 201 based on the time at which the peak pressure measurement is made at each location 210 and 211 and the known distance 602 between sensors 106 according to equation (1). It should be noted that the velocity of pulse wave 201 can be calculated in any manner in accordance with the needs of the application. For instance, velocity measurement system 102 can be configured to analyze the temporal variation in blood pressure at each location 210 and 211 and determine the associated Fourier spectrum. These spectrums can be used to determine the change in phase at each frequency, which translates into a velocity measurement for each frequency.

Figure 8:
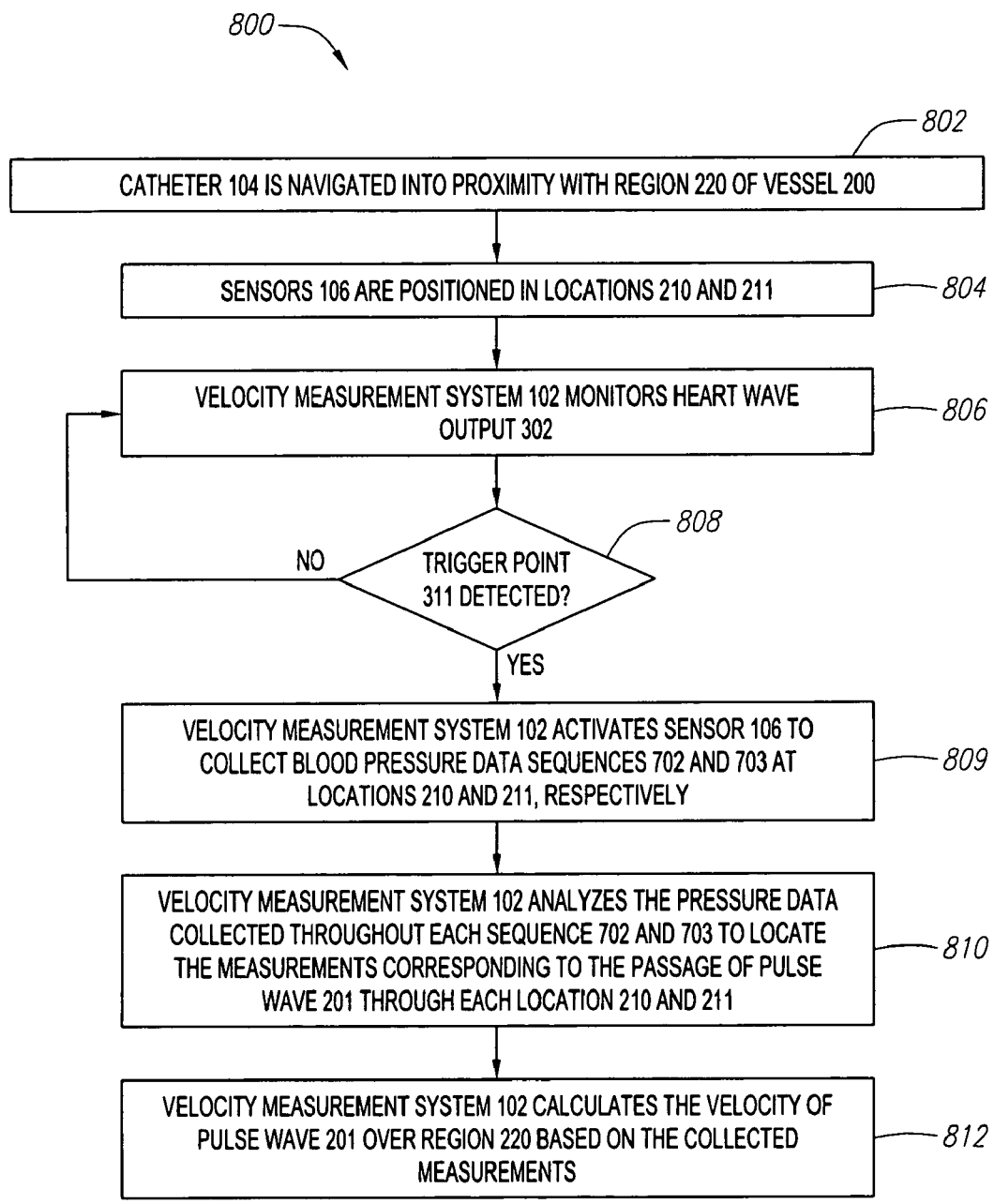
FIG. 8 depicts a flow chart of an example method of measuring pulse wave velocity with an sensor-based method.

FIG. 8 depicts a flow chart of one example of a sensor-based data collection method 800 performed with the embodiment of medical system 100 discussed with reference to FIG. 6A. At 802, catheter 104 is navigated into proximity with the target segment 220 of vessel 200. Then, at 804, sensors 106 are positioned in locations 210 and 211 by sliding central core 206 in a proximal or distal direction as necessary. At 806, velocity measurement system 102 monitors heart wave output 302. Next, at 808, system 102 checks for trigger point 311 in output 302. If trigger point 311 has not occurred, system 102 proceeds back to 806, If trigger point 311 has occurred, system 102 proceeds to 809 and activates sensor 106 to collect blood pressure data sequences 702 and 703 at locations 210 and 211, respectively. Then, at 810, velocity measurement system 102 analyzes the pressure measurements throughout each sequence to locate the measurements corresponding to the passage of pulse wave 201 through each location 210 and 211. Finally, at 812, velocity measurement system 102 calculates the velocity of pulse wave 201 over region 220 based on the collected measurements.

Figure 9:
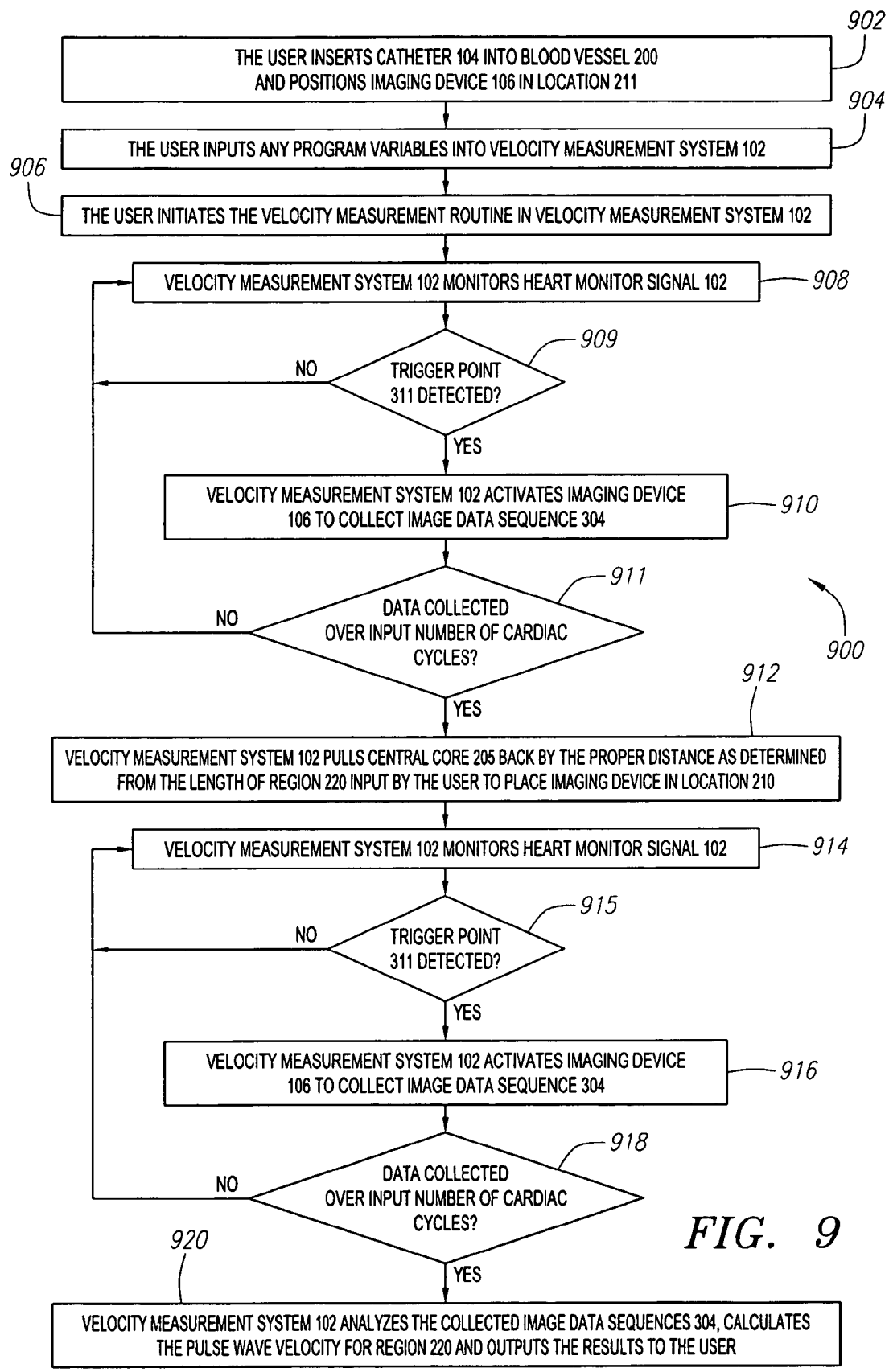
FIG. 9 depicts a flow chart of another example method of measuring pulse wave velocity.

FIG. 9 depicts a flow chart of an example method 900 of measuring the pulse wave velocity using an imaging-based method, where the data collection and velocity calculation steps are performed automatically. At 902, the user or operator inserts catheter 104 into blood vessel 200 and positions imaging device 106 in location 211, using either an external imaging technique such as X-ray or fluoroscopy, or by using imaging device 106 itself. Next, at 904, the user inputs any program variables into velocity measurement system 102. These variables are dependent on the needs of the application. For instance, the user can input the length of region 220, the length of data sequence 304 and the number of cardiac cycles during which medical system 100 will take velocity measurements at each location 210 and 211. Then, at 906, the user initiates velocity measurement routine in velocity measurement system 102.

Once initiated, velocity measurement system 102 monitors heart monitor signal 102 at 908 and checks for trigger point 311 at 909. If trigger point 311 has not occurred, then velocity measurement system 102 proceeds back to 908. If trigger point 311 has occurred, velocity measurement system 102 activates imaging device 106 to collect image data sequence 304 at 910. Then, at 911, velocity measurement system 102 checks if data has been collected over the number of cardiac cycles input by the user. If not, velocity measurement system 102 proceeds back to 908. If the number of cardiac cycles has been met, then velocity measurement system proceeds to 912.

At 912, velocity measurement system 102 pulls central core 205 back by the proper distance as determined from the length of region 220 input by the user to place imaging device in location 210. Then, at 914, velocity measurement system 102 again monitors signal 102 and, at 915, velocity measurement system 102 checks for trigger point 311. If trigger point 311 has not occurred, then velocity measurement system 102 proceeds back to 914. If trigger point 311 has occurred, velocity measurement system 102 activates imaging device 106 to collect image data sequence 304 at 916. Next, 918, velocity measurement system 102 checks if data has been collected over the number of cardiac cycles input by the user. If not, velocity measurement system 102 proceeds back to 914. If the number of cardiac cycles has been met, then velocity measurement system proceeds to 92, where velocity measurement system 102 analyzes the collected image data sequences 304, calculates the pulse wave velocity for region 220 and outputs the results to the user.

In the embodiments discussed above, medical system 100 is used to measure the velocity of a cardiac pulse wave 201 propagating within the subject's various blood vessels 200. System 100 can be referred to as a passive technique because the pulse waves 201 are generated naturally by the subject's heart. However, one of skill in the art will recognize that velocity measurements can be taken using an active technique, where pulse waves 201 are generated artificially and propagated along the desired body lumen or within the desired body tissue. Artificial pulse waves 201 could be generated with a source external to the subject, or with an internal source, such as with a generation device located on catheter 104 and the like. When an active technique is used, the pulse wave generation source is preferably controlled by velocity measurement system 102 to allow coordination of the pulse wave generation and measurement processes.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A method of measuring the velocity of anatomical pulse waves propagating within a body lumen, comprising:
    collecting data from a first anatomical pulse wave with an intravascular device at a first location within a body lumen, wherein the intravascular device is located within the body lumen, and wherein the anatomical pulse wave data collected at the first location comprises image data of an inner wall of the body lumen at the first location;
    collecting data from a second anatomical pulse wave with the intravascular device at a second location within the body lumen, wherein the intravascular device is located within the body lumen, and wherein the anatomical pulse wave data collected at the second location comprises image data of the inner wall of the body lumen at the second location;
    wherein the anatomical pulse wave data collected at the first and second locations are collected upon the occurrence of trigger points; and
    calculating the velocity of anatomical pulse waves in the region between the first and second locations with the anatomical pulse wave data collected at the first and second locations, wherein the velocity of the anatomical pulse waves are calculated based, at least in part, on the difference in time durations between the occurrence of the first trigger point and the collection of anatomical pulse wave data at the first location and the occurrence of the second trigger point and the collection of anatomical pulse wave data at the second location;
    wherein the anatomical pulse wave data collected at the first location and the anatomical pulse wave data collected at the second location are collected from different anatomical pulse waves.

2. The method of claim 1, further comprising calculating the velocity of the anatomical pulse waves along a longitudinal axis of the body lumen.

3. The method of claim 2, further comprising visually mapping the velocity of the anatomical pulse waves along the longitudinal axis of the lumen.

4. The method of claim 1, further comprising calculating the velocity of the anatomical pulse waves along the circumference of the body lumen.

5. The method of claim 1, wherein calculating the velocity of the anatomical pulse waves comprises:
    analyzing the image data to determine the temporal variation of the size of the lumen wall at the first and second locations; and
    calculating the velocity of the anatomical pulse waves based on the temporal variation of the lumen wall at the first and second locations.

6. The method of claim 5, wherein the anatomical pulse waves are heart pulse waves and the body lumen is a blood vessel.

7. The method of claim 6, further comprising monitoring heart pulse wave output signals prior to collecting data at the first and second locations.

8. The method of claim 6, wherein the heart pulse wave data collected at the first location comprises a first sequence of images of the vessel wall at the first location and the heart pulse wave data collected at the second location comprises a second sequence of images of the vessel wall at the second location.

9. The method of claim 8, wherein the trigger points occur within the heart pulse wave output signal.

10. The method of claim 6, wherein the images in each sequence are collected at fixed intervals.

11. The method of claim 6, wherein the images in each sequence are collected at variable intervals.

12. The method of claim 1, wherein the anatomical pulse wave data collected at the first location comprises pressure data within the body lumen at the first location and wherein the anatomical pulse wave data collected at the second location comprises pressure data within the body lumen at the second location.

13. The method of claim 12, wherein calculating the velocity of the anatomical pulse waves comprises:
    analyzing the pressure data at the first and second locations; and
    calculating the velocity of the anatomical pulse waves based on the pressure data at the first and second locations.

14. The method of claim 13, wherein the anatomical pulse waves are heart pulse waves, the body lumen is a blood vessel and the pressure data is blood pressure data.

15. The method of claim 14, further comprising monitoring heart pulse wave output signals prior to collecting data at the first and second locations.

16. The method of claim 15, wherein the heart pulse wave data collected at the first location comprises a first sequence of blood pressure measurements at the first location and the heart pulse wave data collected at the second location comprises a second sequence of blood pressure measurements at the second location.

17. The method of claim 16, wherein the blood pressure measurements in each sequence are collected at fixed intervals.

18. The method of claim 16, wherein the blood pressure measurements in each sequence are collected at variable intervals.

19. The method of claim 16, wherein the trigger points occur within the heart pulse wave output signal.

20. The method of claim 1, wherein the anatomical pulse wave data collected at the first and second locations are collected during different cardiac cycles.

21. The method of claim 20, further comprising:
collecting the anatomical pulse wave data at the first location using a transducer during a cardiac cycle;
repositioning the transducer at the second location; and
collecting the anatomical pulse wave data at the second location using the transducer during a subsequent cardiac cycle.

22. The method of claim 1, wherein collecting anatomical pulse wave data with an intravascular device at a first location within a body lumen and collecting anatomical pulse wave data with the intravascular device at a second location within the body lumen comprises the first location and the second location being at different locations from one other along a longitudinal length of the body lumen.

23. The method of claim 1, wherein the velocity of the anatomical pulse waves are calculated based, at least in part, on a change in phase at one or more frequencies of a Fourier spectrum associated with the temporal variation of body lumen area at the first location and at the second location.

24. A medical system for measuring the velocity of anatomical pulse waves propagating within a body lumen, comprising:
an elongate medical device configured for insertion into the body lumen and comprising a data collection device configured to collect data on anatomical pulse waves propagating along the body lumen and output the data to a velocity measurement system, wherein the anatomical pulse wave data comprises image data of an inner wall of the body lumen; and
the velocity measurement system is communicatively coupled with the data collection device and configured to control the data collection device, wherein the velocity measurement system is configured to calculate the velocity of the anatomical pulse waves propagating along the body lumen based on the collected anatomical pulse wave data, wherein the anatomical pulse wave data is collected at a first location upon the occurrence of a first trigger point and at a second location upon the occurrence of a second trigger point, wherein the second location is a known distance from the first location, wherein the velocity of the anatomical pulse waves are calculated based, at least in part, on the difference in time durations between the occurrence of the first trigger point and the collection of anatomical pulse wave data at the first location and the occurrence of the second trigger point and the collection of anatomical pulse wave data at the second location, and wherein the anatomical pulse wave data collected at the first location and the second location are collected from different anatomical pulse waves.

25. The system of claim 24, wherein the elongate medical device comprises an elongate tubular member having an inner lumen configured to slidably receive a central core member, and wherein the imaging device is located on the central core.

26. The system of claim 25, wherein the velocity measurement system is configured to analyze the image data to determine the temporal variation of the vessel wall and calculate the velocity of the anatomical pulse waves between two locations in the vessel based on the temporal variation of the vessel wall at each of the two locations.

27. The system of claim 26, wherein the anatomical pulse waves are heart pulse waves and the body lumen is a blood vessel.

28. The system of claim 27, further comprising a heart monitor communicatively coupled with the velocity measurement system and configured to output a heart monitor signal to the velocity measurement system.

29. The system of claim 28, wherein the heart monitor is an electrocardiogram unit.

30. The system of claim 28, wherein the velocity measurement system is configured to activate the imaging device to collect a sequence of images of the vessel wall upon the occurrence of trigger points in the heart monitor output signal.

31. The system of claim 24, wherein the data collection device further comprises pressure data from a pressure sensor configured to sense the blood pressure within the vessel and wherein the anatomical pulse wave data is blood pressure data.

32. The system of claim 31, wherein the velocity measurement system is configured to analyze the collected anatomical pulse wave data and calculate the velocity of the anatomical pulse waves between two locations in the vessel based on the blood pressure at each of the two locations.

33. The system of claim 32, wherein the anatomical pulse waves are heart pulse waves.

34. The system of claim 33, further comprising a heart monitor communicatively coupled with the velocity measurement system and configured to output a heart monitor signal to the velocity measurement system.

35. The system of claim 34, wherein the heart monitor is an electrocardiogram.

36. The system of claim 34, wherein the velocity measurement system is configured to activate the pressure sensor to collect a sequence of blood pressure measurements upon the occurrence of trigger points in the heart monitor output signal.

37. The system of claim 24, wherein the elongate medical device further comprises a second data collection device communicatively coupled with the velocity measurement system.

* * * * *